(12) United States Patent
Clayton

(10) Patent No.: US 7,630,474 B2
(45) Date of Patent: Dec. 8, 2009

(54) RADIATION SCANNING WITH PHOTON TAGGING

(75) Inventor: James E. Clayton, Saratoga, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 78 days.

(21) Appl. No.: 11/904,817

(22) Filed: Sep. 28, 2007

(65) Prior Publication Data

US 2009/0086906 A1 Apr. 2, 2009

(51) Int. Cl.
*G01N 23/04* (2006.01)

(52) U.S. Cl. .......................... 378/57; 378/119
(58) Field of Classification Search .................. 378/57, 378/119, 140, 143
See application file for complete search history.

(56) References Cited

U.S. PATENT DOCUMENTS

| | | | |
|---|---|---|---|
| 3,780,291 A | 12/1973 | Stein et al. | |
| 4,342,914 A | 8/1982 | Bjorkholm | |
| 4,745,631 A | 5/1988 | Paolini | |
| 5,181,234 A | 1/1993 | Smith | |
| 5,367,552 A | 11/1994 | Peschmann | |
| 5,524,133 A | 6/1996 | Neale et al. | |
| 5,638,420 A | 6/1997 | Armistead | |
| 5,642,394 A | 6/1997 | Rothschild | |
| 5,903,623 A | 5/1999 | Swift et al. | |
| 5,917,880 A | 6/1999 | Bjorkholm | |
| 6,236,709 B1 | 5/2001 | Perry et al. | |
| 6,269,142 B1 | 7/2001 | Smith | |
| 6,272,206 B1 | 8/2001 | Bjorkholm | |
| 6,278,115 B1 | 8/2001 | Annis et al. | |
| 6,292,533 B1 | 9/2001 | Swift et al. | |
| 6,347,132 B1 | 2/2002 | Annis | |
| 6,414,317 B1 | 7/2002 | Francke et al. | |
| 6,438,201 B1 | 8/2002 | Mazess et al. | |
| 6,628,745 B1 | 9/2003 | Annis et al. | |
| 6,965,661 B2 | 11/2005 | Kojima et al. | |
| 7,095,820 B2 | 8/2006 | Sokolov | |
| 7,103,137 B2 | 9/2006 | Seppi et al. | |
| 7,257,188 B2 | 8/2007 | Bjorkholm | |
| 2004/0141587 A1 | 7/2004 | Arques et al. | |
| 2007/0003003 A1 | 1/2007 | Seppi et al. | |
| 2007/0241282 A1 | 10/2007 | Clayton et al. | |

OTHER PUBLICATIONS

James Edward Clayton, "High Energy Gamma Ray Production in Proton Induced Reactions at Energies of 104, 145 and 195 MeV"; Dissertation for the Degree of Ph. D.; Michigan State University, Department of Physics and Astronomy, 1991, USA.

McDonald, Marci; "Checkpoint Terror Border Searches Snarl the Free Flow of Goods" U.S. News and World Report, p. 52, Feb. 11, 2002.

Grodzins, Lee; Nuclear Techniques For Finding Chemical Explosives In Airport Luggage; Beam Interactions With Materials and Atoms; May 1991; p. 829-833; vol. B56/57, Part II; Elsevier Science Publishers B.V. (North-Holland); Holland.

*Primary Examiner*—Edward J Glick
*Assistant Examiner*—Mona M Sanei
(74) *Attorney, Agent, or Firm*—Brandon N. Sklar, Esq.; Kaye Scholer LLP

(57) ABSTRACT

In accordance with an embodiment, a method of examining contents of objects comprises accelerating a plurality of electrons to a predetermined acceleration energy and colliding the accelerated electrons with a target. An object is scanned with the generated X-ray photons. First energies of X-ray photons are determined after scanning and second energies of accelerated electrons are determined after colliding with the target, and correlated. Energies of respective detected X-ray photons prior to scanning are determined based, at least in part, on the second energies of respective correlated accelerated electrons and the predetermined acceleration energy. A potential presence of suspect material is determined based, at least in part, on the first energies of respective X-ray photons after scanning and the third energies of the detected X-ray photons prior to scanning. Systems are also disclosed.

25 Claims, 2 Drawing Sheets

RADIATION SCANNING WITH PHOTON TAGGING

FIELD OF THE INVENTION

Radiation scanning of objects, including large objects such as cargo containers, using tagged photons to identify the potential preserved.

BACKGROUND OF THE INVENTION

Radiation generated by the impact of a charged particle, such as an electron, on a target, such as tungsten, referred to as Bremsstrahlung radiation, is commonly used in the non-invasive inspection of contents of objects, such as luggage, bags, briefcases, cargo containers, and the like, to identify hidden contraband at airports, seaports, and public buildings, for example. The contraband may include hidden guns, knives, explosive devices, illegal drugs, hazardous chemicals, hazardous biological agents, and weapons of mass destruction, such as a nuclear or a "dirty" radioactive bomb, for example. One common inspection system is a line scanner, where the object to be inspected is passed between a stationary source of radiation, such as a beam of gamma ray radiation or X-ray radiation, and a stationary detector. The radiation transmitted through the object is detected and measured. Radiographic images of the contents of the object may be generated based on the detected radiation after scanning. The images may show the shape, size, and varying densities of the contents. Contraband materials, including special nuclear materials, conventional explosives, and drugs, may thereby be potentially identified. The smuggling of contraband onto planes, as well as the smuggling of contraband across borders and by ship in large cargo containers, are serious threats.

Standard cargo containers are typically 20-50 feet long (6.1-15.2 meters), 8 feet high (2.4 meters), and 6-9 feet wide (1.8-2.7 meters). Air cargo containers, which are used to contain a plurality of pieces of luggage or other cargo to be stored in the body of an airplane, may range in size (length, height, width) from about 35×21×21 inches (0.89×0.53×0.53 meters) up to about 240×118×96 inches (6.1×3.0×2.4 meters). Large collections of objects, such as many pieces of luggage, may also be supported on a pallet. Pallets, which may have supporting side walls, may be of comparable sizes as cargo containers. As used herein, the term container is meant to include, but should not be limited to, standard cargo containers, air cargo containers, pallets, luggage, and hand-held carry-ons.

Atomic bombs and "dirty bombs," which may use a conventional trigger and conventional explosion to disperse radioactive material over a wide territory, are examples of nuclear devices that may be smuggled in cargo conveyances and smaller objects. Radioactive, fissionable, fissile, and fertile materials that may be used to manufacture nuclear devices, may also be similarly smuggled in such objects. Fissile materials, such as uranium-235, uranium-233, and plutonium-239, may undergo fission by the capture of a slow (thermal) neutron. Fissionable materials include fissile materials, and materials that may undergo fission by capture of fast neutrons, such as uranium-238. Fertile materials may be converted into fissile materials by the capture of a slow (thermal) neutron. Uranium-238, for example, may be converted into plutonium-239. Thorium-232, for example, may be converted into uranium-233. Fissionable, fissile, and fertile material may be referred to as "nuclear material." These devices often include control and/or trigger electronics, such as timing devices or communications devices, that are used to detonate the explosive and/or trigger the nuclear device.

A variety of techniques are used to locate nuclear devices, nuclear materials, radioactive materials (that may not be nuclear materials), hazardous chemicals, and hazardous biological agents in containers. While manual inspection of the contents of the objects in a container may be effective in identifying hazardous targets, manual inspection is time consuming and costly. Identification of radioactive materials and nuclear devices and other weapons may be accomplished by passive inspection systems, such as a radiation detector.

Active systems that employ radiation to scan cargo and containers are also known. In one example of an X-ray scanning system, U.S. Pat. No. 5,524,133 discloses scanning systems for large objects, such as freight in a container or on a vehicle. In one embodiment, two stationary sources of X-ray radiation are provided, each emitting a collimated fan beam. The sources facing adjacent sides of the freight and the fan beams are perpendicular to each other. A stationary detector array is located opposite each source, on opposite sides of the freight, to receive radiation transmitted through the freight. The material content of the freight may be thereby analyzed. Additional radiation systems for inspecting large cargo are described in U.S. Pat. Nos. 6,292,533, 5,917,880, and 5,638,420, for example.

Likewise, in U.S. Pat. No. 6,347,132 B1, a high energy X-ray inspection system for detecting nuclear weapons materials is described wherein an object is scanned by a high energy X-ray fan beam or pencil beam. To obtain additional information about the contents of the luggage, radiation detectors may be provided to detect scattered radiation, as described in U.S. Pat. No. 5,642,394, for example. Systems may combine detection of scattered radiation with the detection of transmitted radiation.

Additionally, techniques such as computed tomography ("CT") enable the reconstruction of the cross-sectional images of luggage contents, facilitating the identification of the items in the luggage, as discussed in U.S. Pat. No. 5,367,552 for example. CT images also provide higher resolution, greater image contrast and greater sensitivity to characteristics of the object being scanned, than radiographs. Scanning methods, such as CT, may be used to generate detailed images of identified objects for additional investigation.

In contrast to the cargo container size ranges, typical airport scanning systems for carry-on bags have tunnel entrances up to about 0.40×0.60 meters. Scanning systems for checked luggage have travel openings that are only slightly larger. Since only bags that fit through the tunnel may be inspected, such systems cannot be used to inspect cargo containers. The low energies used in typical X-ray luggage and bag scanners, which are typically in the keV range, are also too low to penetrate through the much larger cargo containers. In addition, many such systems are too slow to economically inspect larger objects, such as cargo containers.

The interaction of radiation with material also varies based on the varying effects of Compton scattering and pair production caused by the interaction of the radiation photons of differing energies with the different materials. A ratio of the attenuations of radiation beams detected at two different energy levels may therefore provide further information about the atomic numbers of the material through which the radiation beam passes. Dual energy systems, which scan an object with two radiation beams at different energy levels, may enable better detection of plastic materials and illegal drugs, for example, than single energy systems. U.S. Pat. No.

5,524,133, which is incorporated by reference herein, describes a dual energy technique for identifying contents of an object.

SUMMARY OF THE INVENTION

Attenuation of a radiation beam transmitted through an object is defined as the difference between the initial intensity of the radiation beam $I_o$ and I(t), the detected intensity of the radiation beam after passing through a material with a thickness t. The detected intensity I(t) is equal to:

$$I(t)=I_o e^{-(\mu/\rho)(\rho t)}=I_o e^{-\mu t} \quad \text{(Equation I)},$$

where $\mu$ is the attenuation coefficient and $\rho$ is the density of the material along the path of the radiation beam. Density $\rho$ is present in the intermediate form of Equation I and cancels in the final form of Equation I shown above. Either form may be used. Since elements have unique atomic numbers Z, and attenuation coefficients $\mu$, attenuation may be used to derive information about the material composition of the scanned contents of the objects. Densities $\rho$ may also be used to derive information about the material composition through Equation I. For example, if the initial energy $I_o$ of a radiation beam and the detected energy I(t) of the radiation beam passing through a material are known, attenuation coefficients $\mu$ and optionally densities $\rho$ may be determined by Equation I and correlated with the atomic number of the material, enabling identification of the material. If the radiation beam traverses a plurality of materials in a container, for example, average attenuation coefficients $\mu$ and densities $\rho$ may be determined. Since a container may contain many materials of unknown identities and thicknesses, potential identification of contraband requires solution of a large number of simultaneous equations based on a large number of measurements of the contents of the container.

X-ray radiation may be generated by impacting a target material, such as tungsten, by accelerated charged particles, such as electrons, by the Bremsstrahlung effect. The resulting radiation beam comprises a plurality of photons, each having an energy along a known, continuous distribution of energies up to a peak energy of the charged particles causing the Bremsstrahlung radiation. The energy distribution characteristics of a Bremsstrahlung X-ray beam is typically broad. The initial energy $I_o$ of an individual X-ray photon is therefore typically only known within a broad range. In a linear accelerator with a peak acceleration energy of 6 MeV, for example, an individual X-ray photon may have a very low energy of a few keV, up to the maximum endpoint energy of the electron beam of 6 MeV. Since the initial energy $I_o$ of each photon is unknown, the attenuation experienced by a detected photon and the radiation beam as a whole cannot be precisely determined. A determination of the attenuation coefficients $\mu$, densities $\rho$, and therefore the identity of the materials within the container based on radiation attenuation measurements is, therefore, also typically imprecise. Imprecise attenuation measurements lead to unacceptably high levels of false positives, making the use of such calculations commercially unfeasible.

Embodiments of the invention include methods and systems that determine the initial energy $I_o$ of individual radiation photons used to scan a container. Attenuation measurements and material identification are thereby improved and contraband may therefore be more readily identified. Tagged photons at high energies (MeV), such as greater than about 1 MeV, or from about 4 MeV to about 9 MeV, for example, may be used to more easily identify high atomic number materials, which may be special nuclear material ("SNM"), or shielding for such material, in large containers, such as cargo conveyances, depending on the contents of the container. High energies, such as from about 1 MeV to about 3 MeV may be used with luggage, as well. Tagged photons at low energies (keV), such as about 500 keV and higher, for example, may be useful in identifying SNM or shielding, as well as explosive materials, in smaller containers, such as luggage, for example.

In accordance with one embodiment of the invention, a method of examining contents of objects is disclosed comprising accelerating a plurality of electrons to a predetermined acceleration energy and colliding the accelerated electrons with a target to cause generation of X-ray photons. The method further comprises scanning at least a portion of an object with at least some of the X-ray photons, determining first energies of at least some of the X-ray photons after scanning, and determining second energies of at least some of the accelerated electrons after colliding with the target. The method further comprises correlating respective first energies of respective X-ray photons after scanning with second energies of respective accelerated electrons after colliding with the target and determining energies of respective detected X-ray photons prior to scanning based, at least in part, on the second energies of respective correlated accelerated electrons after colliding with the target and the predetermined acceleration energy. The method further comprises determining whether a suspect material is at least potentially present based, at least in part, on the first energies of respective X-ray photons after scanning and the third energies of the detected X-ray photons prior to scanning.

A suspect material may be determined to be at least potentially present by determining attenuations of respective detected X-ray photons after scanning based, at least in part, on the first energies of the respective detected X-ray photons prior to scanning and the third energies of the detected X-ray photons, and estimating an average atomic number of materials in the scanned portion of the object based, at least in part, on the attenuations.

The first energies of respective accelerated electrons may be determined by deflecting at least some of the respective accelerated electrons toward a first detector by a magnetic field and determining the first energies of the respective accelerated electrons detected by the detector based, at least in part, on a degree of deflection. The first energies of respective accelerated electrons may be determined based, at least in part, on a location where the accelerated electrons strike the detector.

Correlating may comprise determining first times when the detector detects respective accelerated electrons, determining second times when respective X-ray photons are detected after scanning, and correlating respective first and second energies based, at least in part, on respective first and second times. The method may further comprise determining third times when respective X-ray photons are detected by a second detector, before scanning, and correlating respective first and second energies based, at least in part, on respective first, second times, and third times.

The electrons may be accelerated to a predetermined acceleration energy within a narrow energy band. Passage of X-ray photons having an energies below a predetermined energy level, may be blocked prior to scanning. The object may be a cargo container having a thickness of at least four feet (1.2 m), for example. The electrons may be accelerated to a predetermined acceleration energy in the MeV range.

In accordance with another embodiment, a system for examining contents of an object is disclosed comprising means for accelerating a plurality of electrons to a predetermined acceleration energy, means for colliding the accelerated electrons with a target to cause generation of X-ray photons, and means for scanning at least a portion of the object with the X-ray photons. The system further comprises means for detecting energies of X-ray photons after scanning, means for determining energies of respective accelerated electrons after colliding with the target, and means for correlating respective detected energies of X-ray photons after scanning with determined energies of the respective accelerated electrons after colliding with the target. The system further comprises means for determining energies of respective detected X-ray photons prior to scanning based, at least in part, on the determined energies of respective correlated accelerated electrons after colliding with the target and the predetermined acceleration energy. Means for determining whether a suspect material is at least potentially present based, at least in part, on the detected energies of respective X-ray photons after scanning and the determined energies of the detected photons prior to scanning, is also provided.

In accordance with another embodiment of the invention, a system for examining contents of an object is disclosed comprising at least one radiation source comprising an accelerator configured to accelerate electrons to a predetermined energy, and a target. Impact of the accelerated electrons with the target causes generation of X-ray photons to scan an object. At least one first detector is positioned to detect energies of at least some of the photons after scanning. A magnet is configured to generate a magnetic field to deflect the electrons after impacting the target. At least one second detector is provided to detect at least some of the deflected electrons. At least one processor is coupled to the at least one first and second detectors. The at least one processor is configured to determine first energies of respective X-ray photons detected by the first detector, determine second energies of respective electrons detected by the first and second detectors, after the respective electrons impact the target, and correlate first energies of respective X-ray photons with second energies of respective detected electrons. The processor is also configured to determine third energies of the respective detected X-ray photons prior to scanning based, at least in part, on the determined second energies of respective correlated electrons and the predetermined acceleration energy, and provide an output indicative of the potential presence of suspect material based, at least in part, on the first energies of respective X-ray photons and the third energies of the respective X-ray photons prior to scanning.

The at least one processor may be configured to provide an output by generating an image indicative of the potential presence of suspect material based, at least in part, on the first and third energies. A third detector may be provided between the target and a position of the object during scanning, to detect passage of respective X-ray photons and the at least one processor may be further configured to determine respective third times of passage of respective X-ray photons and correlate respective first and second energies based, at least in part, on respective first, second, and third times. A filter may be provided between the target and third detector to block passage of photons below a predetermined energy. The second energies of respective electrons may be proportional to the location where the at least one electron impacts the electron. The radiation source may be configured to accelerate electrons to a predetermined energy in the MeV range. The accelerator may be configured to accelerate the electrons to a predetermined acceleration energy within a narrow energy band. The system may be configured to examine an object having a thickness of at least four feet.

In accordance with another embodiment, a method is disclosed comprising accelerating a plurality of charged particles to a predetermined acceleration energy, colliding the accelerated charged particles with a target to cause generation of radiation photons, and scanning at least a portion of an object with at least some of the radiation photons. The method further comprises determining first energies of radiation photons after scanning, determining functions of the energies of respective accelerated charged particles after colliding with the target, detected within predetermined time periods, and correlating respective first energies of radiation photons after scanning with respective functions of the energies of the respective accelerated charged particles after colliding with the target. The method further comprises determining approximate second energies of respective radiation photons prior to scanning based, at least in part, on the functions of the energies of respective correlated accelerated electrons after colliding with the target and the predetermined acceleration energy, and providing an output based, at least in part, on the approximate second energies of respective radiation photons prior to scanning and respective first energies of the photons after scanning.

The function may be an average. The predetermined time periods may be from about 2 microseconds to about 10 microseconds long. The method may further comprise determining approximate attenuations of respective radiation photons after scanning based, at least in part, on the first energies of respective radiation photons after scanning and the approximate second energies of respective radiation photons prior to scanning, and providing an output based, at least in part, on the approximate attenuations.

DESCRIPTION OF THE PREFERRED EMBODIMENTS

Embodiments of the invention include a method of and a system for radiation scanning of objects with "tagged" X-ray photons of known energies for the at least potential identification of suspect material, such as SNM, shielding for SNM, and other contraband, in which the initial energies $I_o$ of X-ray photons attenuated by the contents of the object are determined within narrower energy bands than typically available. Attenuation measurements based on such "tagged" photons may be used to provide more accurate determinations of attenuation coefficients $\mu$ and densities $\rho$ of single materials traversed by the photons or average attenuation coefficients $\mu$ and densities $\rho$ of multiple materials traversed by the photons, thereby enabling more accurate determinations of atomic numbers (or average atomic numbers) and identification of materials within objects under inspection.

Furthermore, since the energies of individual photons in a Bremsstrahlung radiation beam vary along a distribution, the resulting tagged photons have known, varying energies, enabling the object to be scanned at a plurality of known energies. This provides more varied data from which the attenuation coefficients $\mu$ and densities $\rho$ of the materials along the photon path, which also improves material identification. In addition, since each measurement has less uncertainty and provides more data, fewer total measurements are required and fewer simultaneous equations need to be solved. The false positive rate may thereby be reduced. Calculation speed and power may also be reduced, as may the radiation exposure of the object and surroundings. Reduction in radiation exposure may be advantageous to the contents and integrity of the container, as well as to operators of the system, others in the vicinity of the system, and castaways, for example. The narrow energy band may be from about 75 keV to about 300 keV or from about 100 keV to 200 keV, for example, for a 9 MeV peak energy accelerator, for example.

In one example, photons are tagged by correlating the electrons causing generation of an X-ray photon in time with the resulting X-ray photons, to determine the initial energy $I_o$ of a photon. The final energy I(t) of the photon after passing through the thickness t of the object under examination is determined by measuring the energy of the detected photon after it passes through the object, in a standard way.

Figure 1:
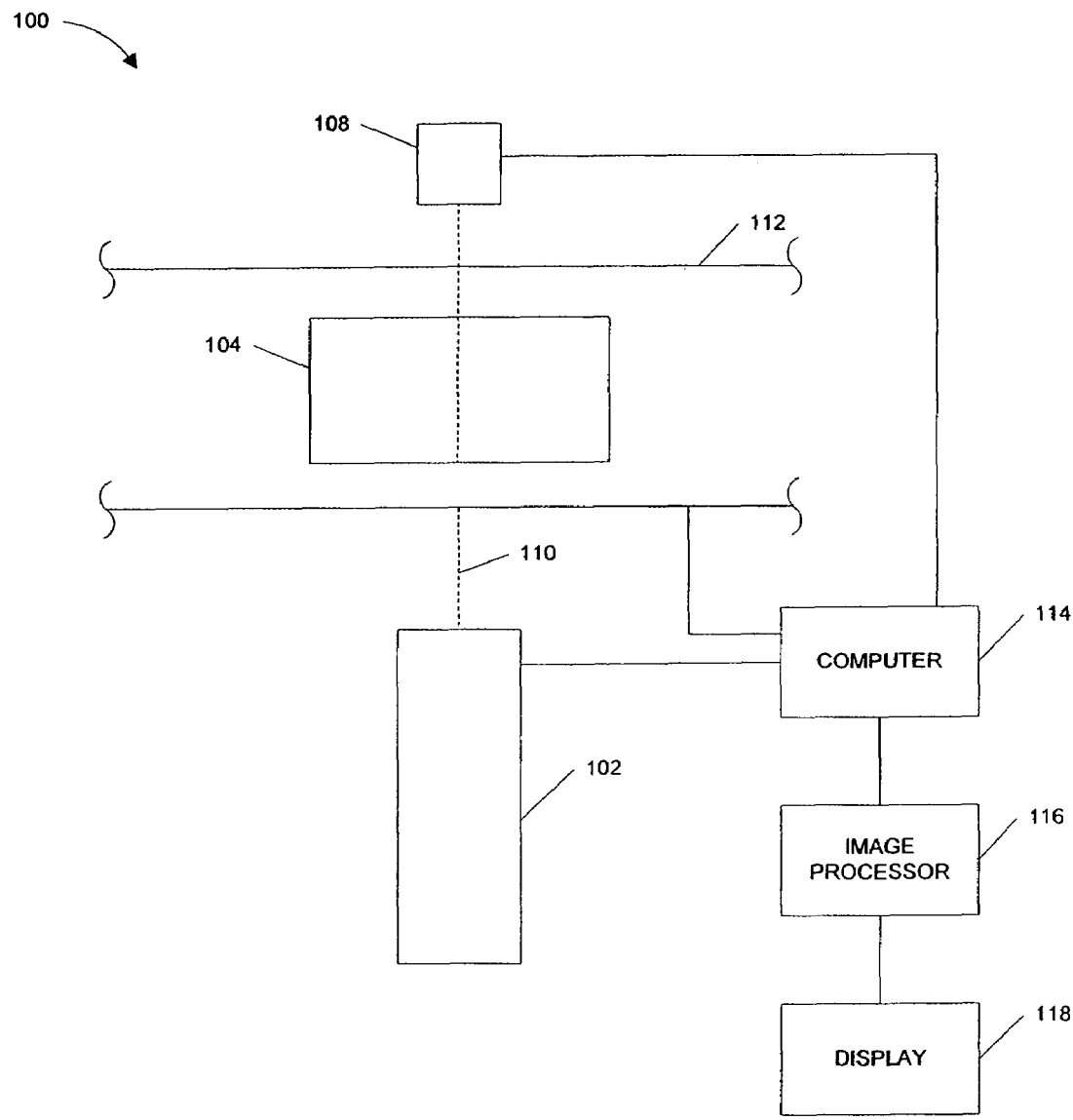
FIG. 1 is a block diagram of a cargo scanning system in accordance with embodiments of the invention.

FIG. 1 is a schematic representation of a top view of an example of a radiation inspection system 100 that incorporates an embodiment of the invention. A tagged photon radiation source 102 is shown on one side of an object to be examined for contraband, such as SNMs and shielding for SNMs, such as a container 104. The tagged photon radiation source 102 may be configured to generate a pencil beam 110 of radiation photons, such as X-ray photons. The energies of at least certain of the X-ray photons are determined to within a narrow energy band, as discussed further below. A detector 108 in this example is positioned on an opposite side of the container 104, to detect the radiation transmitted through the container. The detector 108 may be configured to detect the tagged photons and photons resulting from interaction of the tagged photons (also referred to herein as "tagged photons") with the materials within the container, to determine the attenuation of the tagged photons as they pass through the container 104. The container 104 is supported and moved by a conveyor 112, to move the container 104 through the pencil beam. The radiation source 102 and the detector 108 are coupled to a processor, such as a computer 114. The computer 114 is coupled to an image processor 116, which is coupled to an image display 118. Additional processors or computers may be provided. The image processor 116 may be incorporated in the computer 114 or other such processor, as well. System 100 is merely exemplary and embodiments of the invention may be incorporated into other radiation scanning configurations.

The radiation source 102 may be configured to conduct pencil beam scanning in manners known in the art. For example, the radiation generated from the impact of the electron beam on a target may be collimated into a fan beam that is collimated by a rotating chopper wheel or other such rotating collimator device with a plurality of slits, into a pencil beam that scans across a horizontal or vertical line. Such a pencil beam is referred to as a "flying spot" in the art. Flying spot and other scanning pencil beam configurations are described in U.S. Pat. Nos. 6,278,115 B1, 6,272,206 B1(rotating cylinder with chordal passages), U.S. Pat. Nos. 6,269,142 B1, 5,903,623 (rotating wheel with radial slots and a radiation source at the center), U.S. Pat. Nos. 5,181,234, 4,745,631 (helical slits through a rotating cylinder), U.S. Pat. Nos. 4,342,914, and 3,780,291, which are incorporated by reference herein. Alternatively, electrons may be deflected onto a long target by a magnetic field, as shown in U.S. Pat. No. 6,628,745 B1, which is incorporated by reference herein. The resulting radiation beams may be collimated into a series of pencil beams by a stationary collimator with a plurality of slots, as described in U.S. Pat. No. 6,278,115 B1, which is also incorporated by reference herein.

Figure 2:
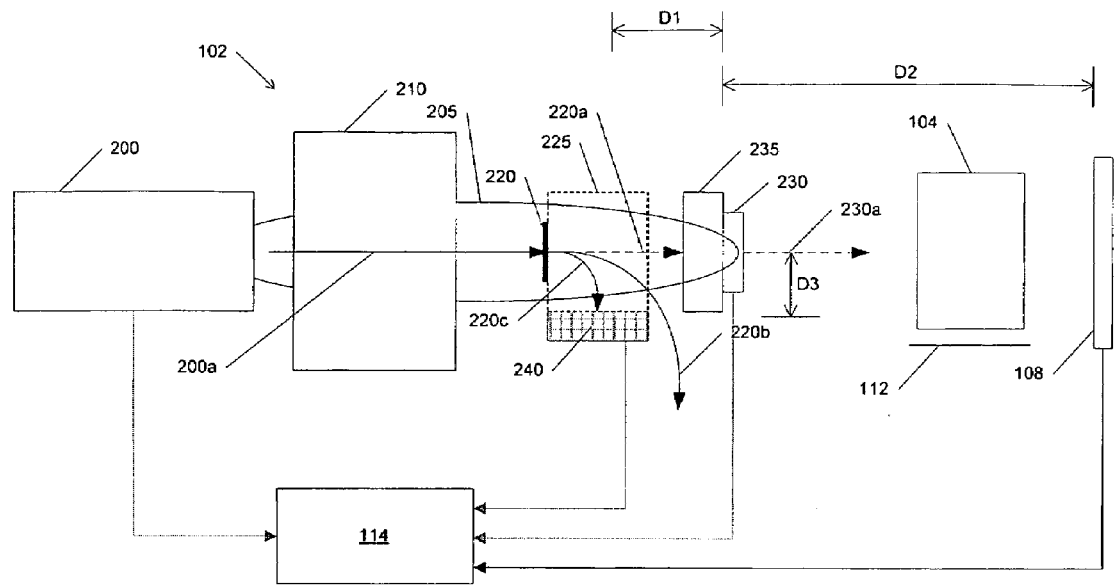
FIG. 2 is a schematic diagram of a tagged photon radiation source in accordance with embodiments of the invention.

The radiation source 102 in the example of FIG. 1 is configured to generate a vertical scanning pencil beam 110, while the container 104 is moved horizontally by the conveyor 112. The detector 108 in this case may be a one-dimensional detector array positioned vertically, as shown in FIG. 2.

Alternatively, the radiation source 102 may be configured to generate a horizontally scanning pencil beam 110, in which case the container 104 may be moved vertically by a platform (not shown) associated with the container 104, through the pencil beam 110. The detector 108 in that case may be a one-dimensional detector array positioned horizontally.

Although only one radiation source is shown, the system 100 of FIG. 1 may include additional radiation sources, including traditional radiation sources, as discussed further below. Some or all of the other radiation sources may define other shaped beams such as fan beams, cone beams, and/or other known beams of tagged or not tagged photons.

The container 104 may be a cargo conveyance, such as a standard cargo container or pallet having a width of 6-9 feet (1.8-2.7 meters) and a length of 20-40 feet (6.1-12.2 meters), for example. The container 104 may also be an alternatively shaped and sized container or other objects, such as air cargo containers, pallets, boxes, or luggage, for example.

The detector 108 may comprise detector array modules comprising one or more scintillators, for example. Scintillators comprising sodium iodide oxide, barium fluoride, or bismuth germanium oxide, with efficiencies if from about 80% to about 90% may be used, for example. Suitable scintillator detectors are available from Saint Gobain Crystals, Houston, Tex., for example. The computer 114 or other such processor may determine the energies of detected photons after transmissions through the container 104 by pulse height analysis, for example, as is known in the art. Data may be provided to the image processor 116, to generate images on the display 118. If other conventional radiation sources or radiation sources 102 in accordance with embodiments of the invention are provided, additional detectors 104 may be provided, as well.

The conveyor system 112 may include a belt, track, rollers, or other such devices, fabricated from a material that causes low attenuation of radiation so that the conveyor system 112 does not interfere with the scanning of the container 104, as is known in the art. The container 104 may be conveyed by a conveyor system 112 through a shielded tunnel positioned between the source 102 and the detector 108, as is also known in the art. The conveyor system 112 may be reversed to reexamine a portion or the container 104 or to scan the entire container 104 again.

One or more computers 114 may be electrically coupled to the detector 104, the conveyor system 112, and/or the source 102. The one or more computers 114 may be configured to control the operation of the X-ray source 102, the detector 104, the conveyor system 108, the image processor 116, and/or the display 118. It would be apparent to one skilled in the art that other configurations for the processing components may also be used.

FIG. 2 is a schematic representation of a side view of the X-ray scanning system 100 of FIG. 1, showing the photon tagging radiation source 102 in more detail, in accordance with an embodiment of the invention. The container 104 supported on the conveyor 112 and the vertical detector 108 are also shown.

The source 102 may include an electron gun (not shown) that provides electrons to an accelerator 200 configured to accelerate the electrons and provide the accelerated electrons into a drift tube 205, under vacuum, as is known in the art. A target 220 is provided within the drift tube 205. The electrons may be focused along a path 200a by a quadrupole magnet (triplet) 210, for example, such that the electron impacts the target 220. One or more radiation photons are generated from respective electrons as the electrons are decelerated by the target material.

The target 220 may comprise tungsten, tantalum, gold, silver, or molybdenum or some other high, density, high atomic number material or combination thereof, for example. The drift tube 205 passes through a magnetic spectrometer 225, which is downstream of the target 220, as discussed in more detail, below.

The accelerator 200 may be configured to accelerate electrons to a peak energy in the MeV range to scan large containers and generate radiation that will transmit through the container 104. For example, to scan cargo conveyances having a thickness of 4 feet (1.2 m) to about 9 feet (2.7 m), or greater, the accelerator 200 may be configured to accelerate electrons to a peak energy from about 4 MeV to about 9 MeV. To scan smaller containers, lower energies may be used. As is known in the art, the optimum energy for scanning depends on both the thickness and the contents of the container 104.

To induce photofission, tagged photons of higher energies, such as from about 15 MeV to about 20 MeV, may be used, for example. The higher energies may be used to induce photofission if suspect material is found in a first scan conducted with or without tagged photons at lower energies. Photofission is described, for example, in U.S. patent application Ser. No. 11/070,032, which was filed on Feb. 28, 2005, is assigned to the assignee of the present invention, and is incorporated by reference herein.

The accelerator 200 may be a type of accelerator that accelerates electrons to a predetermined energy within a narrow energy band, such as from 50 keV to 100 keV wide, for example. In one example, the accelerator 200 may be a long pulse width and/or a high-duty factor accelerator to spread the photons in time. The pulse width may be hundreds of microseconds, for example. The duty factor, which is equal to the rep-rate of an accelerator multiplied by the pulse width of the electrons, may be about 20%, for example. A Rhodotron®, available from IBA Group, Louvain-la-Neuve, Belgium, includes a high rep-rate and may be configured to accelerate electrons to a peak energy in the MeV range, such as a peak energy greater than 1 MeV, or a peak energy in a range from about 4 MeV to 9 MeV, for example. Alternatively, the accelerator 200 may be a DC accelerator, a microtron, or a superconducting radiation accelerator, for example, which are also known in the art.

In one example, the accelerator 200 is configured to accelerate electrons to a peak acceleration energy of 9 MeV and the container 104 is a cargo container 6 feet (1.8 m) thick. The target 220 is thin, so that at the peak acceleration energy of the accelerator 200, most of the electrons pass through the target 220 without generating Bremsstrahlung X-ray photons. A tungsten target having a thickness of from about 0.01 cm to about 0.026 cm and a density of about 19.3 g/cm$^3$ may be used, for example. If the electron current of the electron gun is 1 microamp, for example, about 6.24×10$^{12}$ electrons per second will impact the target 220. In this example, only a few thousand electrons per second (a few kilohertz) will cause generation of Bremsstrahlung X-ray photons of the desired higher energies sufficient to be transmitted through standard cargo containers the container, such as from about 4 MeV to about 9 MeV, for example, depending on the contents of the container. As discussed above, the X-ray photon energies generated by the electrons typically vary over a broad range of energies from a few keV, for example, to energies approaching the energy of the accelerated electron prior to impacting the target.

The generated photons follow a path 220a, through the spectrometer 225 and out of the source 102, towards a container 104 to be examined, as shown in FIG. 1. In accordance with one embodiment of the invention, the energies of the individual photons are determined by determining the energies of the electrons causing generation of the respective photons, after each photon is generated. In this example, the magnetic spectrometer 225 is configured to deflect electrons along curved paths 220b, 220c toward an electron detector or sensor 240, by a magnetic field. The magnetic field may be generated by one or more permanent magnets. Electromagnets may also be used instead of or along with permanent magnets, which may facilitate adjustment of the magnetic field, if necessary. Suitable magnets for the spectrometer 225 may be obtained from SIGMA PHI, Vannes, France, and Danfysik A/S Mollehaven, Denmark, for example. Permanent or electromagnets generating magnetic fields of about 0.065 Tesla may be used with electrons accelerated to a peak energy of 9 MeV, for example.

The amount of curvature experienced by each electron in the magnetic field is a function of the energy of the electron after exiting the target 220. Since the target 220 is thin, as discussed above, most of the electrons impacting the target 220 will pass through the target, retaining substantially all of their energy gained during acceleration. The spectrometer 225 is configured to provide a magnetic field that is too weak to sufficiently deflect these electrons to impact the sensor 240. These electrons will curve downward, away from the filter 235 and the detector 230 and toward the sensor 240, but their energy will carry them beyond the sensor 240, along a path 220b, to an electron dump (not shown). The dump may be sufficiently removed or shielded from the sensor 240 so that the sensor 240 is not exposed to background noise from the dump.

Electrons that do cause generation of X-ray photons have reduced velocity due to the Bremsstrahlung effect. The spectrometer 225 is configured to provide a magnetic field that will deflect most of the electrons that cause generation of X-ray photons along a path, such as path 220c, toward the sensor 240. The sensor 240 provides signals indicative of the energy of the detected electron to the computer 114. The computer 114 determines the energy of the detected electron and the detection time $t_1$. The sensor 240 may be coupled to another processor to make this determination, instead of the computer 114, if desired. The computer 114 may determine the energy of the detected electron by pulse height analysis, for example.

The sensor 240 may comprise one or more scintillators, for example. The initial energy $I_o$ of each photon may be determined to a value within a bandwidth of the energy that is dependent on the pixel size and lateral depth of the sensor 240. As discussed above, the bandwith may be from about 75 keV to about 300 keV, or from about 100 keV to about 200 keV, for a 9 MeV accelerator, for example. The smaller the bandwidth the more precise the determinations. An example of a sensor 240 is discussed in detail below with respect to FIG. 3.

Knowledge of the energy of the electron after generation of a photon enables the energy of the photon ("$E_{photon}$") or photons resulting from Bremsstrahlung of that electron in the target to be determined by the law of conservation of energy, as follows:

$$E_{photon} = E_{einitial} - E_{efinal},\qquad\text{(Equation II)}$$

where $E_{photon}$ is the energy of the photon, $E_{einitial}$ is the initial energy of the electron after acceleration by the accelerator 200, and $E_{efinal}$ is the energy of the electron after causing generation of the Bremsstrahlung X-ray photon, as measured by the sensor 240. Since the accelerator accelerates electrons to an energy within a narrow band, as discussed above, the initial energy $E_{einitial}$ of the electron is known within a narrow band. The detected energy of the electron after Bremsstrahlung $E_{efinal}$ may also be determined to within a desired narrow range by the sensor 240 (as discussed below). The energy of the photon $E_{photon}$ can thereby also be determined within a narrow range.

A generated X-ray photon follows the photon path 220a along an axis X of the radiation source 102, through a thin photon detector 230, which detects the passage of the photon through the detector 230 but only causes a small drop in the energy of the photon. The detector 230 may be a plastic or thin inorganic scintillator with a low efficiency, such as from about 10% to about 15%, for example. A Saint Gobain BC 400, available from Saint Gobain, Solon, Ohio, for example, may be used, for example. The detector 230 is also coupled to the computer 114 or other such processor. When the photon is detected, the detector 230 provides a signal to the computer 114, which determines a detection time $t_2$.

A low energy filter 235 may be provided in front of the photon detector 230, to capture and block passage of low energy photons that do not have enough energy to completely penetrate the thickness of the container 104 being examined, and are not, therefore, needed. Such an optional filter decreases the exposure of the container 104 to unnecessary radiation. For example, if the container 104 is a cargo conveyance 6 feet (1.8 m) thick, radiation photons having energies less than about 500 keV, for example, would probably not completely penetrate a filled cargo conveyance and would not be detected by the detector 106. In addition, by reducing the number of X-ray photons passing through the detector 230, correlating photons with electrons is facilitated, as described further below. A suitable filter may comprise a low atomic number (Z) material, such as nylon or polyethylene, for example, six (6) inches (15.2 cm) to twelve (12) inches (30.5 cm) thick.

The distance D1 from the center of the sensor 240 to the face of the detector 230, may be from about 1.5 feet (45.7 cm) to about 3 feet (91.4 cm), for example. The distance D2 from the surface of the detector 230 to the face of the detector 108 may be from about 11.5 feet (3.5 m) to about 13.1 feet (4.0 m). For example, the distance D3 between the axis X and the face of the sensor 240 may be 0.25 m to about 0.5 m, for example. These distances are merely exemplary and the detectors 108, 230, and 240 may be separated by different distances.

In order to determine the attenuation of the photon transmitted through the container, the energy of the electron causing generation of that photon has to be matched with the energy of the detected photon. This may be done in a variety of ways, as would be apparent to one skilled in the art. In one example, the computer 114 determines the energy of each individual electron and the times $t_1$ that each electron strikes the sensor 240. Returning to FIG. 1, the detector 108 is also coupled to the computer 114, which determines the energies of the detected photons and their respective detection times $t_3$.

In one example, the face of detector 230 is a distance D1 of 1 meter from the center of the sensor 240, the face of the detector 108 is a distance D2 of 6 meters from the face of the detector 230, and the face of the sensor 240 is a distance D3 of 0.5 m from the axis X, then a radiation photon detected at a time $t_2$ about 5 nanoseconds after a time $t_1$ and a time $t_3$ of about 7.5 nanoseconds of an electron striking the sensor 240, will probably have been generated by the impact of that electron on the target 220. It is noted that since the electron has less energy after causing generation of X-ray radiation, it will be moving more slowly than it moved prior to impacting the target 220, which may be taken into account when determining the correlated time periods. The time periods may be adjusted based on differing path lengths of the collimated pencil beams.

The energy of the electron detected at the time $t_1$ may be used to determine the initial energy of the photon detected at the time $t_2$ and/or $t_3$, and the peak acceleration energy of the accelerator 200 by Equation II, above, for example, as discussed above. The attenuation of that photon after transmission through the container 104 may therefore be determined based on the energy of the photon detected by the detector 108.

The computer 114 may use a leading edge discriminator or a constant (k) fraction discriminator to correlate the electrons and photons, which may be configured to start a new time count each time the sensor 240 is impacted, as is known in the art. A photon passing through the detector 230 and/or being detected by the detector 108 at predetermined times $t_3$ and/or $t_2$, respectively, after the start of each time count was probably generated by the detected electron starting the time count. Since the rate of photon production is low (a few kilohertz, for example, as discussed above), the electrons may be correlated with the photons using standard processors and detectors. In another example, the time $t_2$ is not determined and a photon detected by detector 106 is correlated in time only to an electron detected by the sensor 240. Detection times may be determined by comparison to a clock, as well. If two or more photons are detected at or near the end of an expected time period, secondary photons may have been generated during transmission of the initial photon through the container 104. Such photons can be rejected or correlated with an electron and used in the analysis through a suitable algorithm, as would be apparent to one skilled in the art.

Other time periods may also be correlated, in addition to or instead of the correlations discussed above. For example, a time count may commence when each electron is emitted by the electron gun into the accelerator 200 or exits the accelerator 200. The computer 114 or other such processor may be configured to make these determinations and correlations under the control of software and/or hardware. An application specific integrated circuit (ASIC) may be used, for example.

Figure 3:
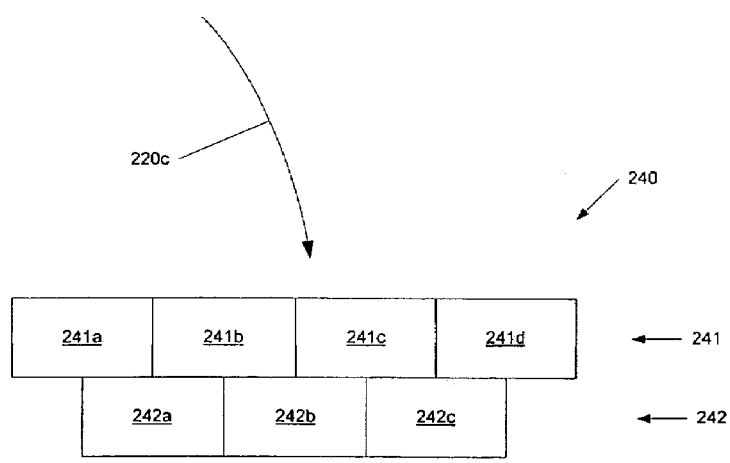
FIG. 3 is a schematic diagram of a sensor that may be used in the radiation source of FIG. 2.

FIG. 3 is a schematic representation of an example of a sensor 240 that may be used in the magnetic spectrometer 225 in accordance with an embodiment of the invention, to measure the energy of a deflected electron. The sensor 240 may be constructed from a series of plastic scintillator plates 241, 242. The location of impact of the electron on the sensor 240 is dependent on the degree of deflection caused by the magnetic field, which is in turn dependent upon the energy (velocity) of the electron after causing generation of a Bremsstrahlung photon by the target.

Each scintillator plate 241, 242 may include a scintillator material that absorbs high energy or charged particle radiation, such as an electron, and, upon absorbing an electron, fluoresces photons, releasing the previously absorbed energy. Each scintillator plate 241, 242 may include an associated photomultiplier or photodiode or other photon or electron sensitive focal plane detectors (not shown), as is known in the art. Consequently, when an individual scintillator plate 241, 242 is hit by an electron, the focal plane detector will detect the light emitted by the scintillator material to identify which scintillator plate has been hit. The focal plane detectors may have a detection resolution of about 100 keV to about 250 keV, or if semiconductor based, a detection resolution of about 10 keV.

Since the degree of deflection of an electron toward the sensor 240 is a function of the energy of the electron, a relatively high energy (high velocity) electron will be deflected less and will therefore strike the sensor 240 closer to the right hand side of the sensor 240 in FIG. 3, near scintillator plate 241d, while a relatively low energy electron will be deflected more and will therefore strike the sensor 240 closer to the left hand side of the sensor 240 in FIG. 3, near scintillator plate 241a. Consequently, the sensor 240 may be calibrated so that the computer 114 or other such processor can correlate the location that the electron-strikes on the scintillator plates with the final energy of the electron. Electronics associated with the sensor 240 may be configured to provide a signal to the computer 114 to indicate which scintillator plate has been hit. As discussed above, the computer 114 determines the time of impact with the sensor 240.

In the example of FIG. 3, the sensor 240 comprises two layers of scintillator plates: an upper layer 241 having scintillator plates 241a, 241b, 241c, 241d and a lower layer 242 having scintillator plates 242a, 242b, and 242c. The two layers 241, 242 of scintillator plates may be stacked and offset as shown in FIG. 2 to increase the resolution that would be provided compared to a single layer 241 of scintillator, without reducing the size of individual scintillator plates (which would be more expensive). For example, detection of the electron by the scintillator plate 242b after it impacted the scintillator plate 241c, would indicate that the plate 241c was actually impacted in portion 241cl. Twenty-five scintillator plates may be provided in each layer, providing 50 detection bins, for example. The difference in energy from one bin to the next may be from about 100 KeV to about 300 KeV, for example.

One or more layers of additional scintillator plates may also be provided with similar offsets, for even greater resolution. Three layers of scintillator plates may improve resolution to one-third of a plate while four layers of scintillator plates may improve resolution to one-quarter of a plate. Also, one layer of smaller scintillator plates may be used instead of or along with the multilayers of FIG. 3. One layer of larger scintillator plates may also be used, with less resolution. The size and shape of the scintillator plates may also be modified.

The detector 240 may comprise sodium iodide, barium fluoride, or bismuth germanium oxide scintillators, for example. In one example, the scintillators for the detector 240 may have an efficiency of from about 80% to about 90%, for example. Suitable detectors are sold by Saint Gobain Crystals, Houston, Tex., for example.

In accordance with embodiments of the invention, tagged X-ray photons may be used in the scanning system 100 shown in FIG. 1 to more accurately identify the attenuation experienced by the tagged X-ray photons and, consequently, the atomic number of a hazardous object using the known initial energy level of the photons and the measured attenuation of the photon by the detector 106.

In an example of a method of generating a tagged X-ray photon for use in the system 100 shown in FIG. 1, electrons are accelerated by the accelerator 200 to a predetermined energy level, such as about 6 MeV. The accelerated electrons strike the target 220 to generate X-ray photons by high energy Bremsstrahlung. The photons are formed into a pencil beam, which passes through the low energy filter 235 and through the photon detector 230, toward the container 106 to scan successive portions of the container 104. Each portion is scanned by a plurality of photons in the pencil beam. The photons transmitted through the container 106 are detected by the detector 108. At least some of the photons may be attenuated by the contents of the container along the path of the photons.

Meanwhile, after generation of each X-ray photon, the electron that generated that photon is deflected by the magnetic spectrometer 225 along a curved path toward the sensor 240. The electron impacts the sensor 240, which provides signals to the computer 114 indicative of the energy of the electron. The computer 114 determines the energy of the electron and the detection time $t_1$.

The detection times $t_2$ of each photon detected by the detector 230 and the detection times $t_3$ of each photon detected by the detector 108 are also determined by the computer 114, which correlates the times $t_1$ of electrons with the times $t_2$ and/or $t_3$ for detected photons to identify the electron which caused generation of a respective photon, based on the times $t_1$, $t_2$ and/or $t_3$ and the distances D1, D2 and/or D3. The detected energy I(t) of the electron is subtracted from the known initial energy $I_o$ of the electron after acceleration by the accelerator 200 to determine the energy of the resulting X-ray photon, by the computer 114. For example, if the sensor 240 detects an electron having a detected energy I(t) of 6 MeV at a time $t_1$, the resulting X-ray photon will have an energy of about 3 MeV (6 MeV-3 MeV). A photon detected by the detector 230 at a time $t_2$ about 5 nanoseconds after the time $t_1$ and then detected at a time $t_3$ about 7.5 nanoseconds later than $t_2$, is considered to be the same photon resulting from the electron.

The initial energy $I_o$ and the detected energy of the tagged photon I(t) may then be used in Equation I, along with many other such Equations with to and I(t) values for other tagged photons traversing the same portion of the container. A sufficient number of such equations based on a sufficient number of tagged photons may then be solved simultaneously to better determine average attenuation coefficients μ and optionally average densities ρ of the materials in those portions of the contents of containers, in a manner known in the art.

For example, the results of the calculations may be compared to tables of correlations of attenuation coefficients μ and densities ρ to materials may be used to better determine the potential material content of the container, also in manners known in the art. The tables may include correlations to pure materials of interest, correlations to varying amounts of mixtures of interest, and/or multilayers of materials of interest having the same or different thicknesses, for example. The materials of interest may include special nuclear materials ("SNMs"), such as uranium and plutonium, and shielding for SNMs, such as tungsten and lead, as well as common acceptable materials, such as iron. Other contraband, such as explosive materials and illegal drugs, may also be included. The knowledge of the initial energies $I_o$ of the tagged photons may enable reduction of the number of possible combinations of materials that could cause the measured attenuations, contributing to the confidence of the potential identification of suspect material.

In addition to better identifying the initial energies $I_o$ of the photons scanning the container, since the photons have energies across the distribution of Bremsstrahlung radiation, embodiments of the invention facilitate multi-energy scanning of containers and other objects and materials. Multi-energy scanning over a Bremsstrahlung radiation distribution may provide additional useful information compared to scanning at a single energy. Embodiments of the invention enable multi-energy scanning without the cost and complexity of multiple radiation sources or energy switching radiation sources (although multiple sources and energy switching radiation sources may be used if desired). The determined attenuations at different energies may be used with dual energy or multiple energy techniques, such as those described in U.S. Pat. Nos. 5,524,133 and 7,257,188, for example, which are incorporated by reference herein. U.S. Pat. No. 7,257,188 is assigned to the assignee of the present invention.

The attenuations and/or correlations may be used to provide more accurate X-ray images through image processing techniques known in the art, such as image segmentation, gradient analysis, and/ratios. Other outputs along with or instead of images that are indicative of the contents of the container 104 may also be provided. For example, potential atomic numbers (z) and/or potential material identifications may be provided in an image or other display or listing. An alarm could also be activated to indicate the potential presence of suspect material.

While discussed with respect to a pencil beam, the source 102 shown in FIG. 2 may be configured to generate a fan beam or other shaped beam by providing a suitable collimator. In that case, the spectrometer 225 may need to be enlarged to be able to measure the electron energies, as would be apparent to one of ordinary skill in the art.

Even if each individual electron causing generation of an X-ray photon is not individually correlated with a resulting X-ray photon, approximate initial X-ray photon energies in an X-ray beam over a short period of time may be determined based on a function of the energies of the electrons detected during that time period, which may be correlated with the photon or photons detected in a corresponding time period after scanning. This may enable more accurate characterization of the initial X-ray energy over that time period than is typically provided in the prior art. The function may be an average, for example. The time period may be from 2 microseconds to 10 microseconds, for example. As above, the calculation of average attenuation coefficients and average densities while reducing the radiation exposure to the container 104, castaways, and operators of the scanning system 100, and others in the vicinity of the scanning system.

In accordance with other embodiments of the invention, traditional scanning systems may be used to initially identify potentially suspect materials. Once a suspect material has been identified for further investigation, a tagged photon radiation source 102 and spectrometer 225 may be used to better identify the suspect material. As discussed above, multiple radiation sources may be used in which one or more of the radiation sources are dedicated to the production of tagged photons while one or more other traditional radiation sources are used in traditional scanning techniques. The traditional scanning techniques may be used to identify suspect containers while embodiments of the invention may be used to scan the suspect containers for more accurate results, for example. Alternatively, a single radiation source may be configured with multiple targets such that the source may operate both as a traditional radiation source and as a source of tagged photons (with a thinner target).

Embodiments of the invention may be used with the detection of scattered radiation in addition to or instead of transmitted radiation.

While embodiments of the invention have been described as being capable of scanning containers such as cargo conveyances, embodiments of the invention may also be used to examine other objects, such as luggage, bags, boxes, etc. Patients may be examined, as well. Furthermore, while the charged particles discussed above are electrons and the generated radiation is X-ray radiation, other charged particles, such as protons and deuterons, may be used to generate other types of radiation, such as tagged neutrons.

The embodiments described herein are examples of implementations of the invention. Modifications may be made to these examples without departing from the scope of the invention, which is defined by the claims, below.

What is claimed is:

1. A method of examining contents of objects, the method comprising:
  accelerating a plurality of electrons to a predetermined acceleration energy;
  colliding the accelerated electrons with a target to cause generation of X-ray photons;
  scanning at least a portion of an object with at least some of the X-ray photons;
  determining first energies of at least some of the X-ray photons after scanning;
  determining second energies of at least some of the accelerated electrons after colliding with the target;
  correlating respective first energies of respective X-ray photons after scanning with second energies of respective accelerated electrons after colliding with the target;
  determining third energies of respective detected X-ray photons prior to scanning based, at least in part, on the second energies of respective correlated accelerated electrons after colliding with the target and the predetermined acceleration energy; and
  determining whether a suspect material is at least potentially present based, at least in part, on the first energies of respective X-ray photons after scanning and the third energies of the detected X-ray photons prior to scanning.

2. The method of claim 1, comprising determining whether the suspect material is at least potentially present by:
  determining attenuations of respective detected X-ray photons after scanning based, at least in part, on the first energies of the respective detected X-ray photons prior to scanning and the third energies of the respective detected X-ray photons prior to scanning; and
  estimating an average atomic number of materials in the scanned portion of the object based, at least in part, on the attenuations.

3. The method of claim 1, comprising accelerating the electrons to a predetermined acceleration energy within a narrow energy band.

4. The method of claim 1, wherein determining the first energies of respective accelerated electrons comprises:
  deflecting at least some of the respective accelerated electrons toward a detector by a magnetic field; and
  determining the first energies of the respective accelerated electrons detected by the detector based, at least in part, on a degree of deflection.

5. The method of claim 4, comprising determining the first energies of respective accelerated electrons based, at least in part, on a location where the accelerated electrons strike the detector.

6. The method of claim 4, wherein correlating comprises:
  determining first times when the detector detects respective accelerated electrons;
  determining second times when respective X-ray photons are detected after scanning; and
  correlating respective first and second energies based, at least in part, on respective first and second times.

7. The method of claim 6, further comprising:
  determining third times when respective X-ray photons are detected by a second detector, before scanning; and correlating respective first and second energies based, at least in part, on respective first, second times, and third times.

8. The method of claim 1, further comprising blocking passage of X-ray photons having energies below a predetermined energy level, prior to scanning.

9. The method of claim 1, wherein the object is a cargo container having a thickness of at least four feet (1.2 m), the method comprising:
scanning the cargo container.

10. The method of claim 1, comprising:
accelerating the elections to a predetermined acceleration energy in the MeV range.

11. A system for examining contents of an object, the system comprising:
means for accelerating a plurality of electrons to a predetermined acceleration energy;
means for colliding the accelerated electrons with a target to cause generation of X-ray photons;
means for scanning at least a portion of the object with the X-ray photons;
means for detecting energies of respective X-ray photons after scanning;
means for determining energies of respective accelerated electrons after colliding with the target;
means for correlating respective detected energies of X-ray photons after scanning with determined energies of the respective accelerated electrons after colliding with the target;
means for determining energies of respective detected X-ray photons prior to scanning based, at least in part, on the determined energies of respective correlated accelerated electrons after colliding with the target and the predetermined acceleration energy; and
means for determining whether a suspect material is at least potentially present based, at least in part, on the detected energies of respective X-ray photons after scanning and the determined energies of the respective detected X-ray photons prior to scanning.

12. A system for examining contents of an object, the system comprising:
at least one radiation source, the source comprising:
an accelerator configured to accelerate electrons to a predetermined energy; and
a target, wherein impact of the accelerated electrons with the target causes generation of X-ray photons to scan an object;
at least one first detector positioned to detect energies of at least some of the X-ray photons after scanning;
a magnet configured to generate a magnetic field to deflect the accelerated electrons after impacting the target;
at least one second detector to detect at least some of the deflected electrons; and
at least one processor coupled to the at least one first and second detectors, the at least one processor configured to:
determine first energies of respective X-ray photons detected by the first detector;
determine second energies of respective electrons detected by the second detector, after the respective electrons impact the target;
correlate first energies of respective X-ray photons with respective second energies of respective detected electrons;
determine third energies of the respective detected X-ray photons prior to scanning based, at least in part, on the determined second energies of respective correlated electrons and the predetermined acceleration energy; and
provide an output indicative of the potential presence of suspect material based, at least in part, on the first energies of respective X-ray photons and the third energies of the respective X-ray photons prior to scanning.

13. The system of claim 12, wherein the at least one processor is configured to provide an output by:
generating an image indicative of the potential presence of suspect material based, at least in part, on the first and third energies.

14. The system of claim 12, wherein the at least one processor is configured to:
determine attenuations of X-ray photons based, at least in part, on the first energies of respective X-ray photons and the third energies of the respective X-ray photons prior to scanning; and
determine an average atomic number of materials in the scanned portion of the object based, at least in part, on the attenuations.

15. The system of claim 12, wherein the at least one processor is further configured to:
determine first times when the first detector detects respective X-ray photons; and
determine second times when the second detector detects respective electrons; and
correlate respective first and second energies based, at least in part, on respective first and second times.

16. The system of claim 14, further comprising:
a third detector between the target and a position of the object during scanning, to detect passage of respective X-ray photons;
wherein the at least one processor is further configured to:
determine respective third times of passage of respective X-ray photons; and
correlate respective first and second energies based, at least in part, on respective first, second, and third times.

17. The system of claim 16, wherein the system further comprises:
a filter between the target and third detector, the filter being configured to block passage of photons below a predetermined energy.

18. The system of claim 12, wherein the magnet and the second detector are configured such that second energies of respective electrons are proportional to the location where each respective electron impacts the second detector.

19. The system of claim 12, wherein:
the accelerator is configured to accelerate electrons to a predetermined energy in the MeV range.

20. The system of claim 12, wherein the accelerator is configured to accelerate electrons to a predetermined energy within a narrow energy band.

21. The system of claim 13, configured to examine an object having a thickness of at least four feet (1.2 m).

22. A method of examining an object, the method comprising:
accelerating a plurality of charged particles to a predetermined acceleration energy;
colliding the accelerated charged particles with a target to cause generation of X-ray radiation photons;
scanning at least a portion of an object with at least some of the radiation photons;
determining first energies of respective radiation photons after scanning;

determining functions of the energies of accelerated charged particles after colliding with the target, detected within predetermined time periods;

correlating respective first energies of radiation photons after scanning with respective functions of the energies of the accelerated charged particles after colliding with the target;

determining approximate second energies of respective photons prior to scanning based, at least in part, on the functions of the energies of respective correlated accelerated electrons after colliding with the target and the predetermined acceleration energy; and providing an output based, at least in part, on the approximate second energies of respective radiation photons prior to scanning and respective first energies of the radiation photons after scanning.

23. The method of claim 22, wherein the function is an average.

24. The method of claim 22, comprising:

determining functions of the energies of the accelerated charged particles after colliding with the target, based, at least in part, on the energies of accelerated charged particles after colliding with the target, detected within time periods from about 2 microseconds to about 10 microseconds long.

25. The method of claim 22, comprising:

determining approximate attenuations of respective photons after scanning based, at least in part, on the first energies of respective radiation photons after scanning and the approximate second energies of respective radiation photons prior to scanning; and providing an output based, at least in part, on the approximate attenuations.

* * * * *